United States Patent [19]

Janese

[11] Patent Number: 5,053,046

[45] Date of Patent: Oct. 1, 1991

[54] DURAL SEALING NEEDLE AND METHOD OF USE

[75] Inventor: Woodrow W. Janese, 2806 N. Navarro, Ste. M, Victoria, Tex. 79901

[73] Assignee: Woodrow W. Janese, Houston, Tex.

[21] Appl. No.: 579,105

[22] Filed: Sep. 6, 1990

Related U.S. Application Data

[63] Continuation of Ser. No. 234,716, Aug. 22, 1988, abandoned.

[51] Int. Cl.⁵ ............................................. A61B 17/04
[52] U.S. Cl. .................................. 606/215; 606/230; 606/213; 604/51
[58] Field of Search ........ 606/213, 215, 216, 228–232; 623/1, 11; 604/51, 60

[56] References Cited

U.S. PATENT DOCUMENTS

| | | | |
|---|---|---|---|
| 3,874,388 | 4/1975 | King et al. | 128/334 R |
| 4,007,743 | 2/1977 | Blake | 128/334 R |
| 4,525,157 | 6/1985 | Vaillancourt | 604/165 |
| 4,705,040 | 11/1987 | Mueller et al. | 128/334 R |
| 4,710,192 | 12/1987 | Liotta et al. | 128/334 R |
| 4,741,330 | 5/1988 | Hayhurst | 606/232 |
| 4,744,364 | 5/1988 | Kensey | 128/334 R |
| 4,852,568 | 8/1989 | Kensey | 623/1 |
| 4,890,612 | 1/1990 | Kensey | 606/213 |

FOREIGN PATENT DOCUMENTS 8701270 3/1987 PCT Int'l Appl. ............. 128/334 R

OTHER PUBLICATIONS

Marton et al., "Reivew of Spinal Taps", *Annals of Internal Medicine*, 1986, 104:840.
Wetchler et al., "A Tehnique to Minimize the Occurance of Headace After Lumbar Puncture by Use of Small Bore Spinal Needles", *Anesthesiology*, 1955, 19:270–281.
Tourtellotte et al., *Post Lumbar Puncture Headaches*, Springfield, C. C. Thomas, 1964, pp. 28, 36.
Shenkin et al., "Clinical Significance of Low Cerebral Spinal Fluid Pressure", *Neurology*, 1958, #3, 157–163.

*Primary Examiner*—Stephen C. Pellegrino
*Assistant Examiner*—Ralph A. Lewis
*Attorney, Agent, or Firm*—Vaden, Eickenroht, Thompson & Boulware

[57] ABSTRACT

A spinal needle which has the capability of sealing its opening after withdrawal. A first conventional spinal needle or cannula is used for standard diagnostic or therapeudic use. A second cannula is inserted concentrically into the first needle and includes a dural seal having an absorbable suture extending from the second cannula. A stylet is inserted into the second cannula dislodging the seal into the subarachnoid space. The cannulae are removed and the suture is pulled to set the dural seal in the spinal puncture.

18 Claims, 8 Drawing Sheets

Fig IIA

Fig IIB

DURAL SEALING NEEDLE AND METHOD OF USE

The application is a continuation of co-pending application Ser. No. 234,716, filed on Aug. 22, 1988, now abandoned.

FIELD OF THE INVENTION

This invention relates to the field of puncturing the subarachnoid compartment of the spine for the purpose of diagnosis and therapeusis. More particularly, the invention relates to the field of medical neurology where the opening caused by the lumbar puncture is plugged to prevent reduction of intraspinal or intracranial cerebrospinal fluid pressure.

BACKGROUND OF THE INVENTION

In the treatment of disease it becomes necessary to obtain a sample of cerebrospinal fluid and/or inject material into the spinal subarachnoid compartment. According to the previous art, after the spinal cannula had been inserted and the procedure performed, the cannula was withdrawn. Fluid inside the subarachnoid space, which is under a pressure of 0.3–1.2 PSI, would then flow through a circular opening the size of 0.397 square mm to 1.26 square mm resulting from the penetration of a needle or cannula of 22 gauge (outside diameter=0.71 mm) or 18 gauge (outside diameter=1.27 mm) respectively across a pressure gradient into the subdural or the epidural compartments and subsequently decrease the intraspinal and/or intracranial cerebrospinal fluid pressure. No apparatuses are known to have been developed to plug this fluid leak. No needles or cannulae are presently marketed which can seal the pia-arachnoid/dura mater to prevent cerebrospinal fluid transfer from the subarachnoid space into the subdural space or epidural space. A "blood patch" (20 cubic centimeters of autologous whole blood) can be performed to prevent post-lumbar headache. After a spinal tap or puncture 20 cc's of a patient's own fresh whole blood is injected by a syringe into the epidural space. The whole blood clots in 4–8 minutes and forms a "patch" to prevent cerebrospinal fluid from leaking; success is irregular and intra-spinal pressure dynamic change is difficult to check. Another method to minimize the mortality and morbidity of the spinal tap is to minimize the needle diameter size to 26 gauge 0.457 mm diameter); this small sized needle requires a pressure transducer for pressure readings and usually a pump for fluid withdrawal.

The spinal tap can cause death by cerebral herniation through the tentorial notch and/or foramen magnum. The spinal tap can also cause sudden irreversible paraplegia. The spinal tap in a series of over 500 patients increased the risk of death 1000% in patients with increased intracranial pressure without papillaedema, fatalities reaching 12% (Marton and Gean, Annals of Internal Medicine, 104:840 (1986)). Complications include: (1) headache; (2) infection; (3) nerve/spinal cord injury; (4) bleeding.

Present indications for performing a spinal puncture are the following: (1) diagnosis of bacterial meningitis; (2) diagnosis of mycobacterial and fungal meningitis; (3) diagnosis of subarachnoid hemorrhage; (4) diagnosis of neoplastic meningitis; (5) diagnosis of viral encephalitis; (6) diagnostic study of myelography; (7) diagnostic study of isotope cisternography. Therapeutic uses of the spinal tap include: (8) subarachnoid steroid injection; (9) cerebrospinal fluid removal as treatment for cerebrospinal fistula; (10) epidural analgesic instillation; (11) epidural block anesthesia; (12) palliative subarachnoid injections for interminable pain.

It is accepted axiomatically that neurological deterioration can result from shifting of intracranial parts caused by intercompartmental pressure gradients or differences. Intracranial and cervical intraspinal fluid pressures have been measured in patients with an enlarging intracranial mass, revealing grossly different pressures in these two compartments. Because of this intercompartmental gradient—high pressure intracranially and low pressure intraspinally—it is considered very dangerous to perform a spinal puncture which would increase the pressure gradient. In one series (Connley E. S., in Yoomans JR. Philadelphia: W. B. Saunders, 5:3196 1982) of 30 patients with an enlarging intracranial mass, the following developed after a lumbar puncture: (1) three—immediate apnea; (2) seven—unequal pupils; (3) twelve—death. This study showed 40% death rate with increased intracranial pressure secondary to an expanding mass.

A pressure gradient can also exist in the spinal canal: spinal tumor produces a complete spinal subarachnoid block causing an intraspinal pressure gradient, i.e., high pressure above mass and low pressure below mass. Sudden paralysis after a spinal puncture below a block can occur—the cerebrospinal fluid below the block having provided a critical buffer. When the cerebrospinal fluid was removed from the subarachnoid space by spinal tap or subsequent dural leak, the spinal cord was compressed by the pressure gradient with physiological function cessation and/or anatomical injury. This phenomenon has been termed "spinal coning" and has been given in incidence of 25%. Even if a small amount of fluid is removed below a spinal pressure gradient, fluid subsequently continues to leak from the subarachnoid compartment into subdural compartment and/or epidural compartment. This deterioration of neurological function of patients with a spinal compartment pressure gradient following a spinal tap has occurred in as short a time as 30 minutes to up to 4 days after the procedure. This later onset attests to the continued leakage of cerebrospinal fluid out of the subarachnoid space aggravating the intraspinal pressure gradient.

SUMMARY OF THE INVENTION

The present invention is directed to satisfying the need for an effective, simple, safe, and economic mechanism to prevent cerebrospinal fluid leakage from the subarachnoid space into the subdural and/or epidural space after a spinal puncture and further to prevent an aggravation of a preexisting intracranial/intraspinal or intraspinal/intraspinal pressure gradient.

Another object of the present invention is the provision of an dural sealing apparatus for spinal puncture and sealing which includes a first cannula and a first stylet for performing a spinal puncture, a second cannula and a second stylet in which the second cannula is telescopically insertable into the first cannula. A dural seal means is positioned in the distal end of the second cannula and the seal includes seal actuating means extending out of the proximal end of the second cannula. The second stylet is telescopically insertable into the second cannula for pushing the seal means out of the second cannula.

A still further object of the present invention is wherein the seal actuating means is a length of absorbable suture.

A still further object of the present invention is wherein the dural seal means includes a dry gelatin product sealing component which softens and swells in the presence of cerebrospinal fluid and can be used to seal the spinal puncture.

Yet a still further object of the present invention is wherein the dural seal means includes silicon elastomer elastic initially folded impact wings for packing the softened gelatin product.

Still a further object of the present invention is wherein the dural seal means includes a silicone elastomer impact cone for seating in a needle puncture for backing up the fluid softened gelatin product and impact wings.

A still further object of the present invention is the provision of an apparatus and method including two concentric cannulae and two respective stylets. The first cannula and stylet perform the standard spinal puncture. When the diagnostic or therapeutic procedure is accomplished, the second cannula is inserted into the first cannula, having a seal extending beyond the outer cannula and bathed in cerebrospinal fluid. This second cannula has an absorbable suture in its lumen which extends through the puncture to the outside of the patient into the sterile field. The stylet of the inner cannula is then inserted, extending beyond the inner cannula and pushing the seal, tethered by the absorbable suture, into the cerebrospinal fluid. The seal absorbs water and swells and the wings forming part of the seal spread. The clinician then waits, gently pulls on the suture until an initial moderate resistance is first felt (an impact cone seats in the arachnoid/dura mater opening); a more firm resistance indicates the impact wings have seated into the cone with the gelatin product in between, both forming a secure plug. The suture which is cut and taped to the skin drops off in a few days.

Other and further objects, features and advantages will be apparent from the following description of a presently preferred embodiment of the invention, given for the purpose of disclosure, and taken in conjunction with the accompanying drawings.

DESCRIPTION OF THE PREFERRED EMBODIMENTS

Figure 1A:
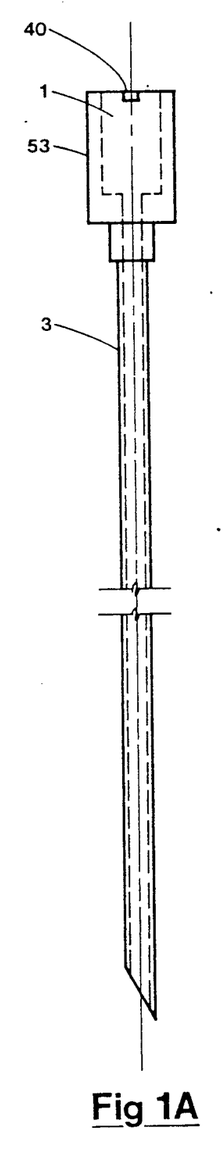
FIG. 1A is a elevational view of a first needle or an outer cannula.
Figure 1B:
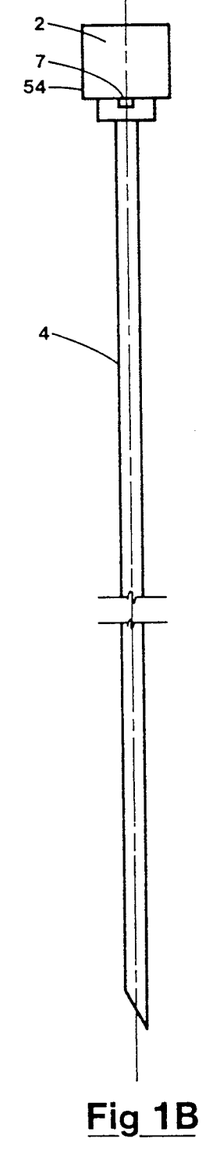
FIG. 1B is an elevational view of a stylet for use with the apparatus of FIG. 1A to perform a standard spinal puncture.

Referring now to FIGS. 1A and 1B, a needle or an outer cannula 1 is shown having a metal tube 3 and a hub 53 having a locking insert opening 40. Stylet 2 includes a rod 4 for insertion into the tube 3 of the needle 1 and includes a hub 54 and a locking insert 7. Preferably, the needle 1 is a standard 18 gauge thin-wall spinal needle (OD of 1.27 mm, ID of 1.09 mm, wall thickness 0.09 mm, and length of 105 mm). The needle 1 and stylet 2 is thus a conventional spinal needle for performing standard diagnostic or therapeutic uses.

Figure 2A:
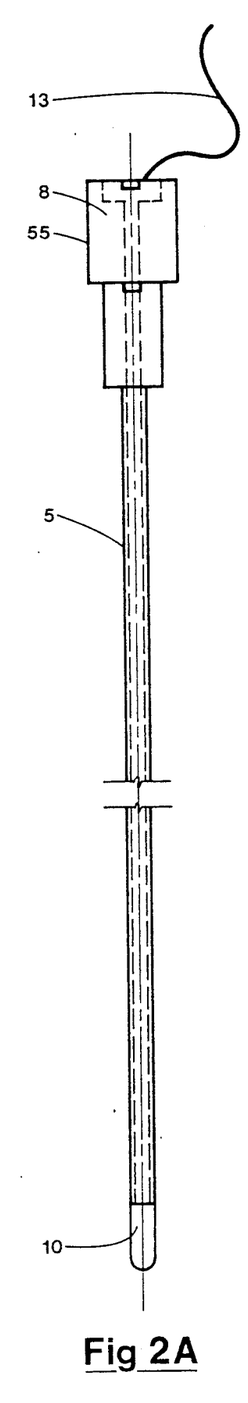
FIG. 2A is an elevational view of a second needle or an inner cannula for use in the outer cannula of FIG. 1A.
Figure 2B:
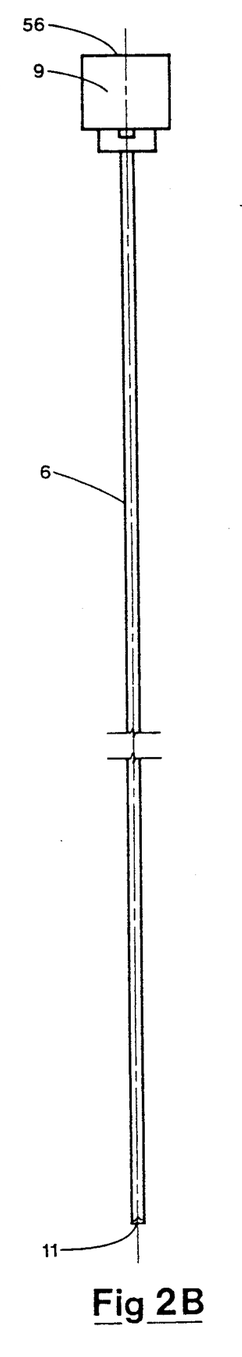
FIG. 2B is an elevational view of the stylet for use with the cannula of FIG. 2A.
Figures 5, 6:
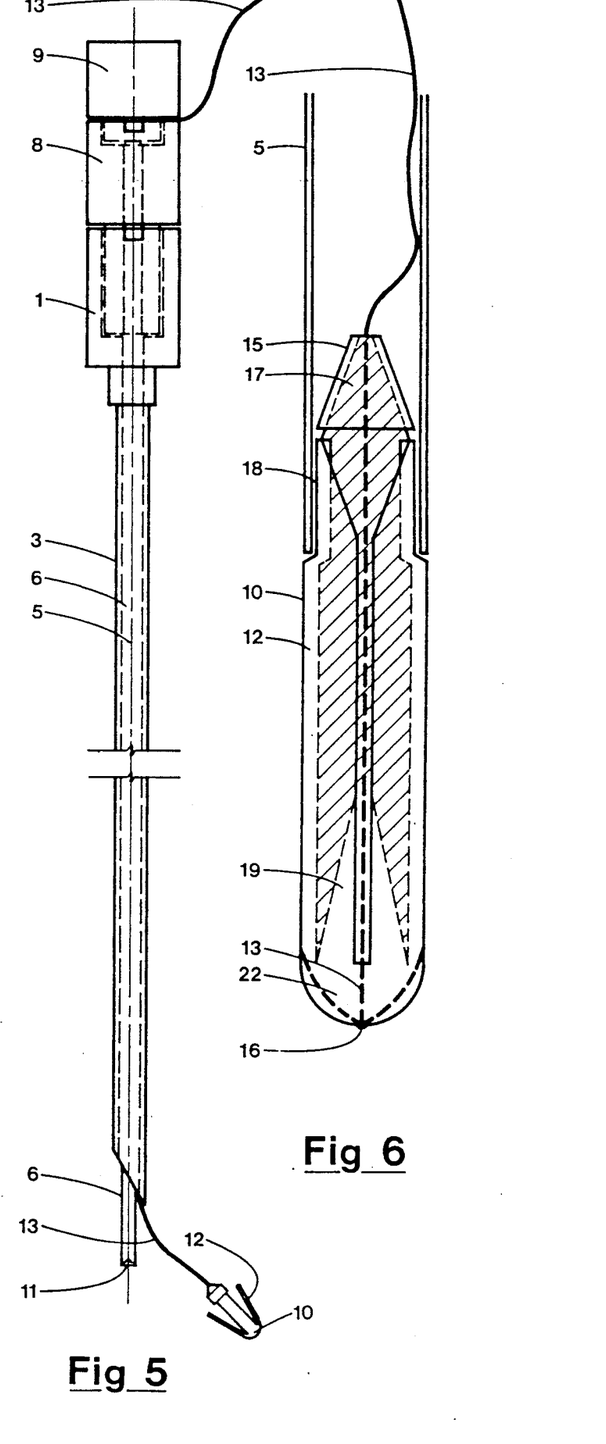
FIG. 5 is an elevational view illustrating the insertion of the stylet of FIG. 2B into the apparatus of FIG. 4.
FIG. 6 is an enlarged elevational view of the positioning of the dural seal in the distal end of the inner cannula of FIG. 2A, FIG. 7A through 7L are cross-sectional views of the apparatus shown in FIG. 6.
Figure 7A:
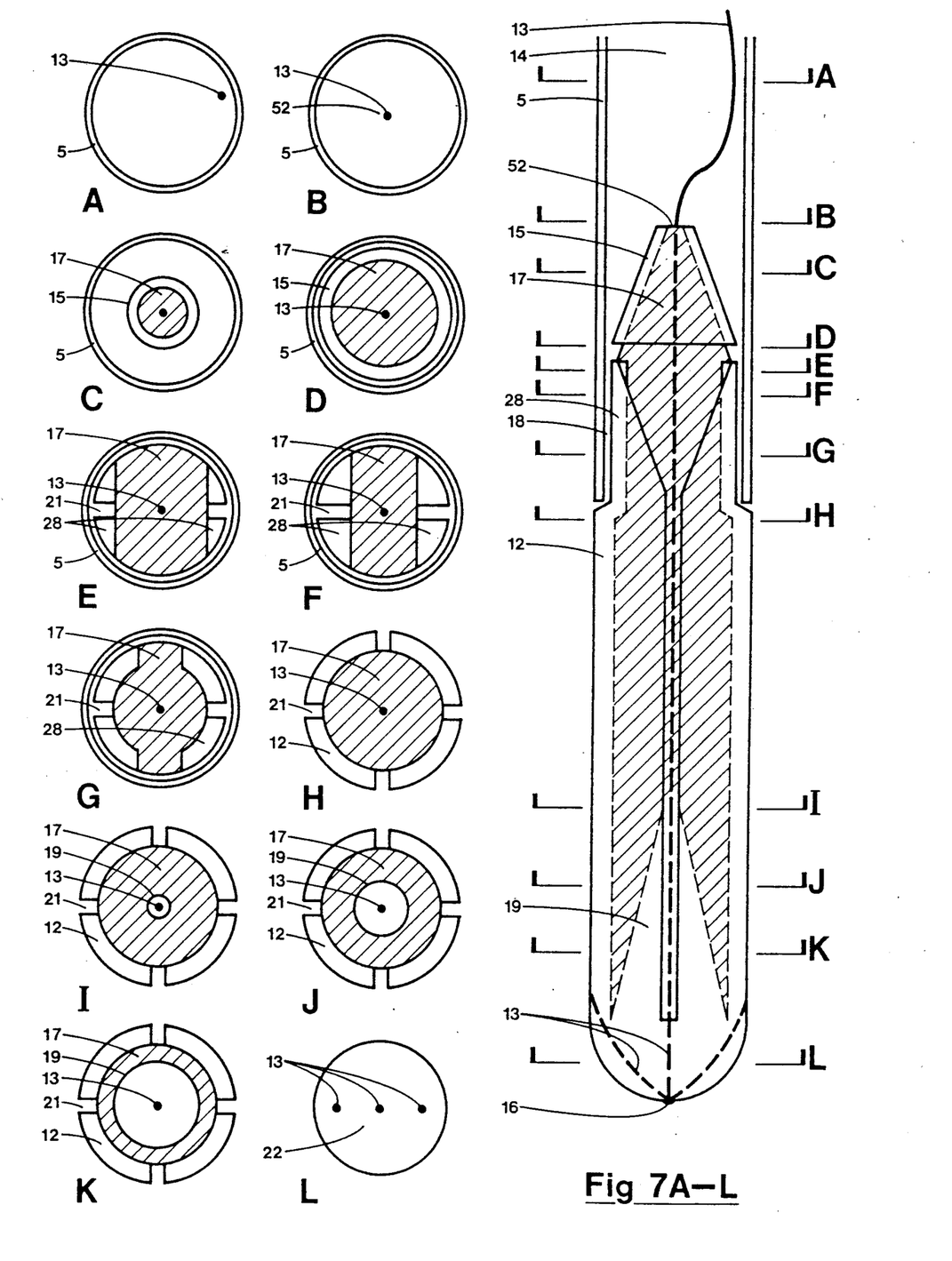
Figure 8:
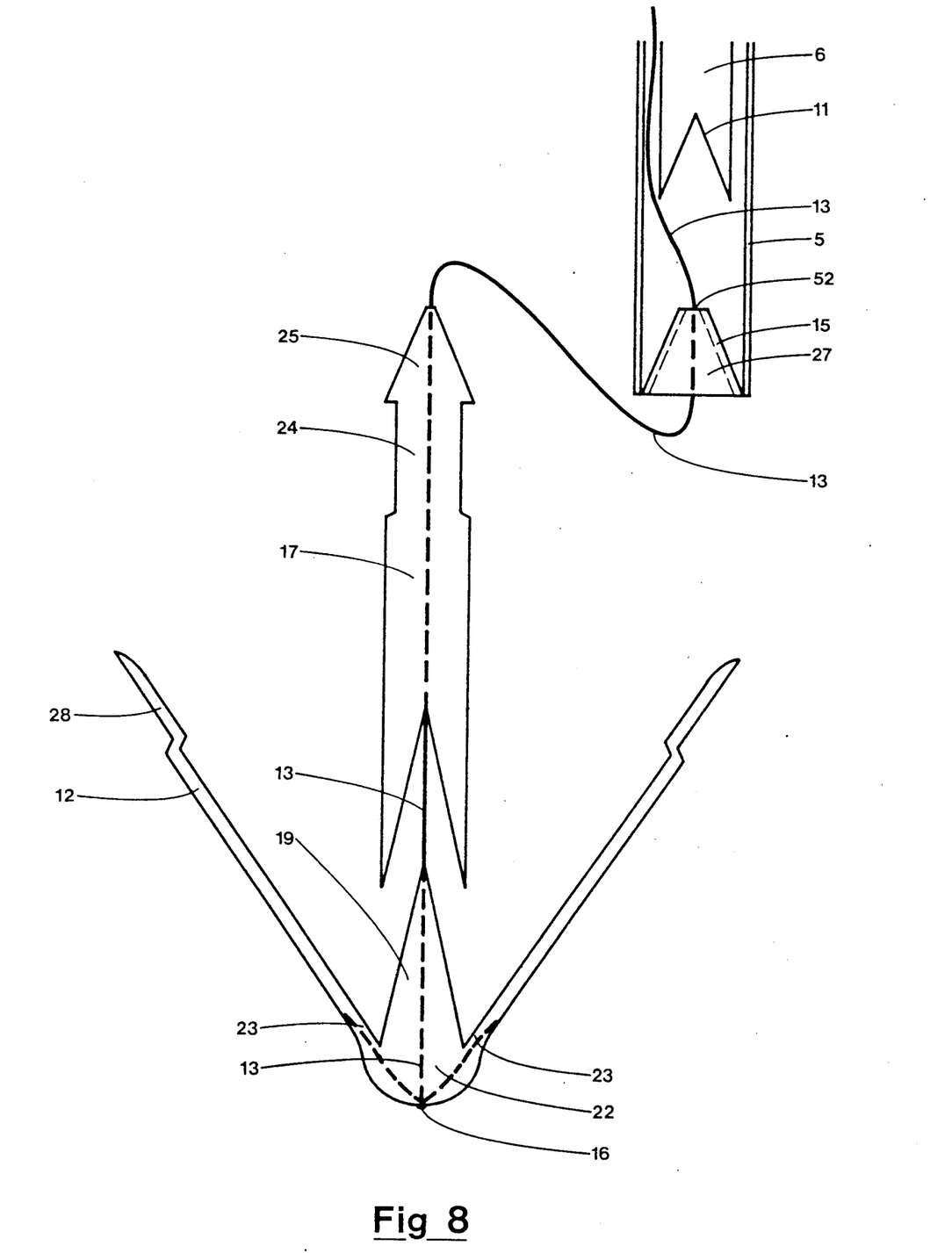
FIG. 8 is an enlarged exploded elevational view illustrating the components of the dural seal.
Figure 9:
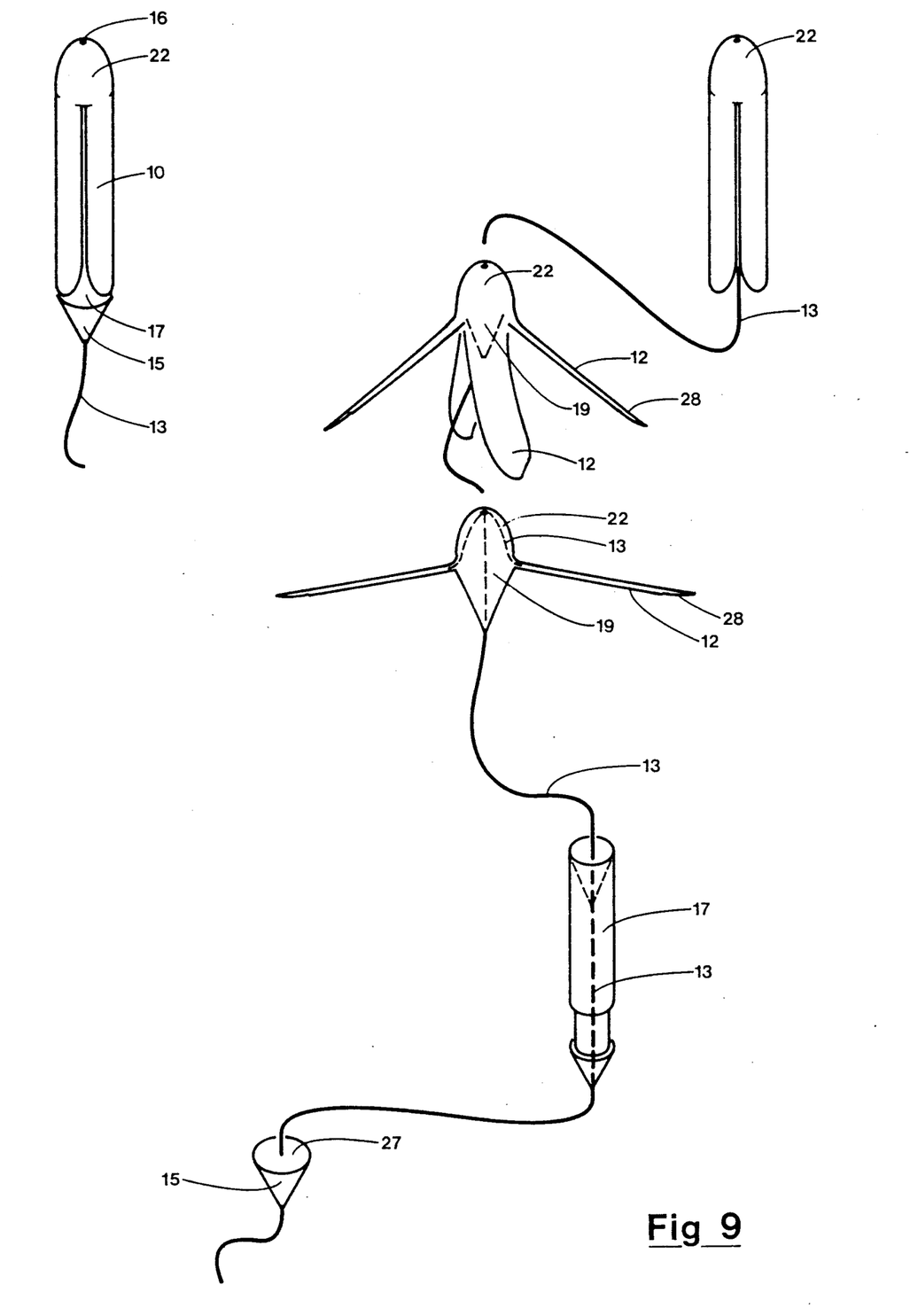
FIG. 9 is a dynamic view of the dural seal of the present invention.

Referring now to FIGS. 2A and 2B, a second needle or cannula 8 includes a tubular member 5 and a hub 55. A needle 8 is adapted to be telescopically and concentrically inserted into needle 1. Inner cannula 8 may have an OD of 1.05 mm, an ID of 0.87 mm, a wall thickness of 0.09 mm, and a length of 119 mm. As shown in FIGS. 2A and 6, the distal end of the tube 5 includes a cleft 18 for holding a dural seal generally indicated by the reference numeral 10. An actuating line 13 is connected to the dural seal means 10 and extends, as best seen in FIG. 2A, out of the proximal end of the outer cannula 8. Preferably, the line 8 is an absorbable suture such as 4-0 caliber. The stylet 9 includes a rod 6 and a hub 56 for insertion into the tube 5 of the needle 8 and includes a specialized shape distal end 11 such as V-shape for pushing the sealing means 10 out of the needle 8.

Figure 3:
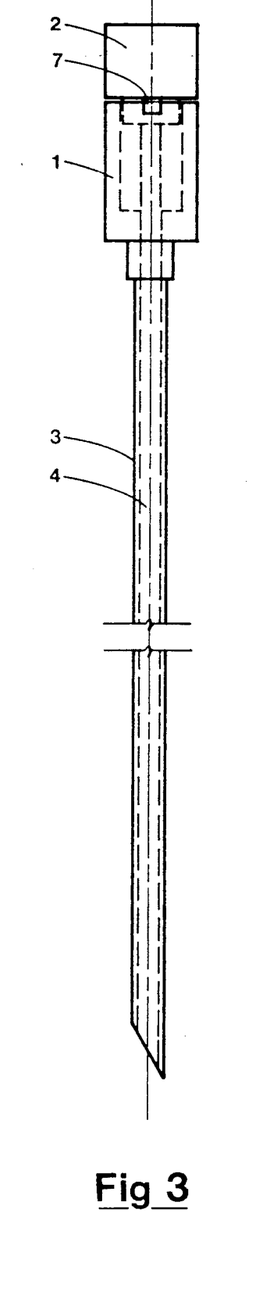
FIG. 3 is an elevational view of the outer cannula of FIG. 1A with the stylet of FIG. 1B inserted therein.
Figure 4:
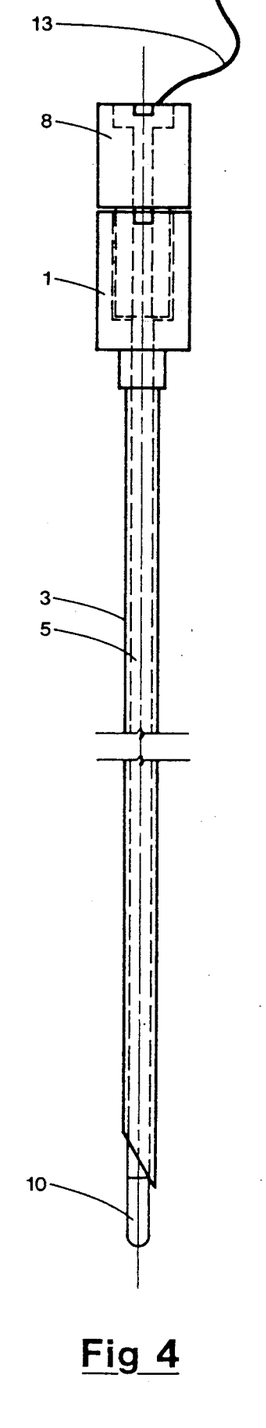
FIG. 4 is an elevational view of the inner cannula of FIG. 2A inserted into outer cannula of FIG. 1A.

Referring now to FIG. 3, the stylet 2 has been inserted into the needle or outer cannula 1 for performing conventional spinal puncture for conventional diagnostic tests or treatment. FIG. 4 illustrates the positioning of the inner cannula or needle 8 into the outer cannula or needle 1 for inserting the dural sealing means 10 attached to the inner needle 8 into the spinal cavity. FIG. 5 shows the insertion of the stylet 9 into the inner cannula 8 for pushing the seal means 10 out into the spinal cavity but retaining control over the seal 10 by the use of the absorbable suture 13.

The dural seal means 10 has the capability of sealing the spinal puncture after withdrawal of the needles 1 and 8 and stylet 9.

Referring now to FIGS. 6, 7A-7L, 8 and 9, the dural sealing means generally includes an impact cone 15, such as a silicone elastomer, which is slidably connected to the suture 13 and generally includes a conical body having a conical interior space 27, a dry gelatin sealing compound 17 slidably connected to the suture 13, and impact wings 12 having a nose 16 secured to the distal end of the suture 13.

The impact cone 15, a seating device retracted into the spinal puncture, provides a seat for the gelatin product 17. The dry gelatin product, internal to the impact wings 12, when pushed into the subarachnoid space is subject to complete cerebrospinal fluid bathing causing the dry gelatin product to soften and swell. When the gelatin product 17 is drawn by tension on the suture 13 towards the impact cone 15, the product 17 acts as a coagulation filler, seats against the cone 15 and seals the puncture. For example, the gelatin product 17 may be of the type sold under the trademark Gelfoam.

The initially folded impact wing assembly 22 is composed of any suitable elastic material such as silicone elastomer. When the sealing means 10 is released from the needle 8, a plurality of wings 12 initially spread outwardly, such as 1 to 2 mm by their intrinsic opening elasticity. The outer parts 28 of the wings 12 turn outward slightly when liberated from the distal end of the needle 8. As tension is applied on the suture 13 against nose 16, the wings 12 are drawn out further by leverage action and by engaging the gelatin product 17, all of which causes the gelatin product to "pancake" and become packed down around the impact cone 15.

The impact wing assembly 22 also preferably includes an impact cone 19 for engaging the interior 27 of the impact cone 15 and seat therein by the action of tension on the suture 13 for securing the gelatin product 17 in place.

Referring now to FIGS. 10A through 10F, the method of using the present invention is best shown. For purposes of anatomical reference, skin 37, subcutaneous adipose tissue 36, deep lumbo-sacral fascia 39, spinous process 31, interspinous ligament 38, dura and pia-arachnoid 35, vertebral body 33, subarachnoid space 30, intervertebral disk 32, and pedicle 34 are shown.

Figure 10A:
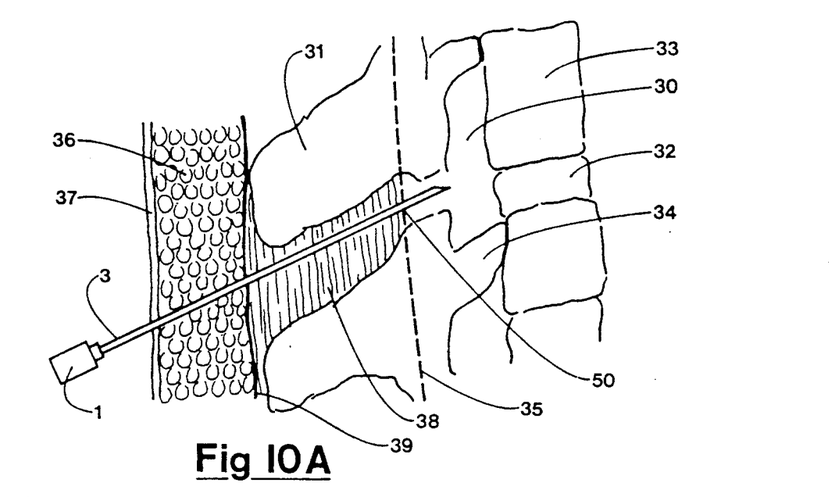
FIG. 10A is an elevational view in cross-section of the outer cannula of FIG. 1A in situ.
Figure 10B:
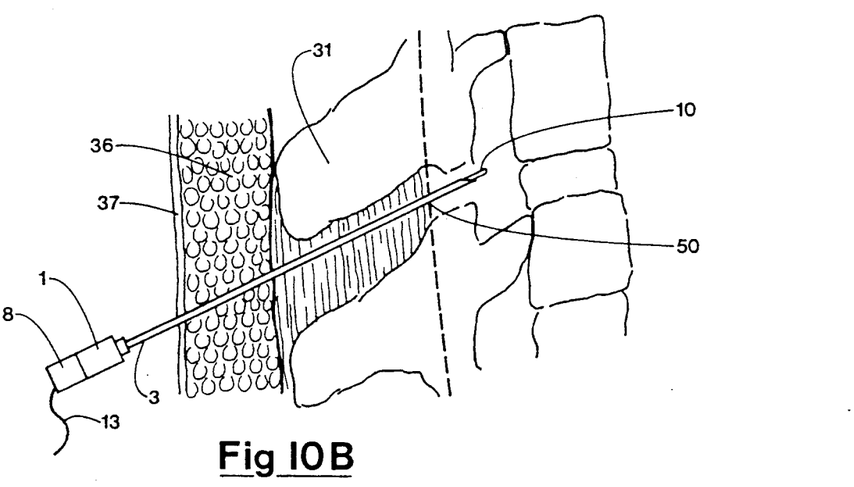
FIG. 10B is a view similar to FIG. 10A with the inner cannula of FIG. 2A inserted into the outer cannula of FIG. 1A.
Figure 11A:
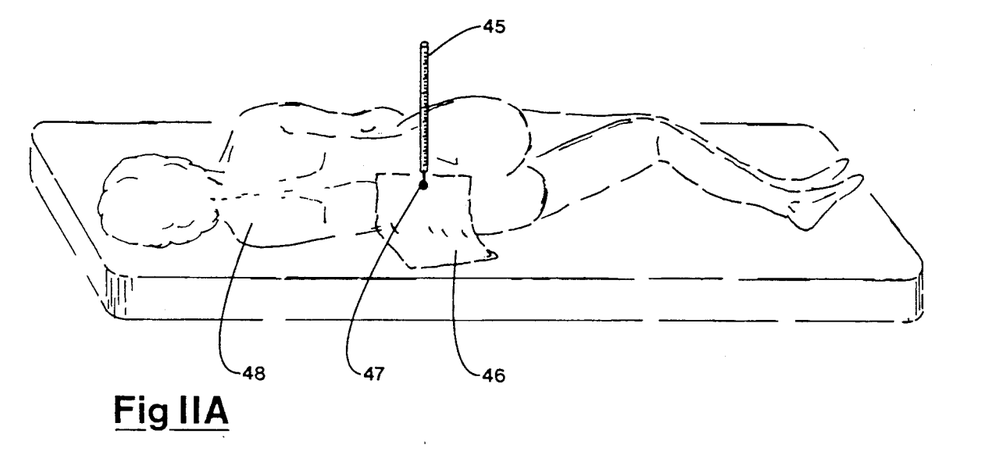
FIG. 11A is an elevational view illustrating a patient having a diagnostic lumbar puncture.

In FIG. 10A, the needle or outer cannula 1 is placed in the subarachnoid space 30 in the usual manner and manometer 45 (FIG. 11A) readings are taken and cerebrospinal fluid samples are sent for protein, glucose, VDRL, and cell count differential. Further diagnostic tests or treatments may then be initiated as indicated.

After the lumbar puncture has been performed, needle or inner cannula 8 is inserted into the outer cannula 1 (FIG. 10B) with the absorbable suture 13 hanging out of the hub 55 of cannula 8. It is noted that the dural sealing means 10, which is carried by the inner cannula 8, is positioned in the space 30.

Figure 10C:
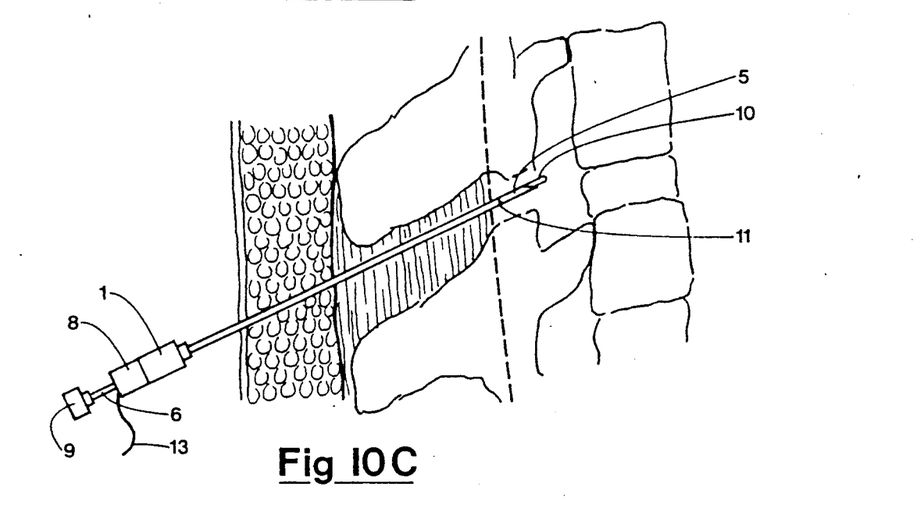
FIG. 10C is a view similar to FIG. 10B with the stylet of FIG. 2A inserted into the cannula of FIGS. 1A and 2A.

In FIG. 10C, the stylet 9 is inserted into the inner cannula 8 while the suture 13 is held.

Figure 10D:
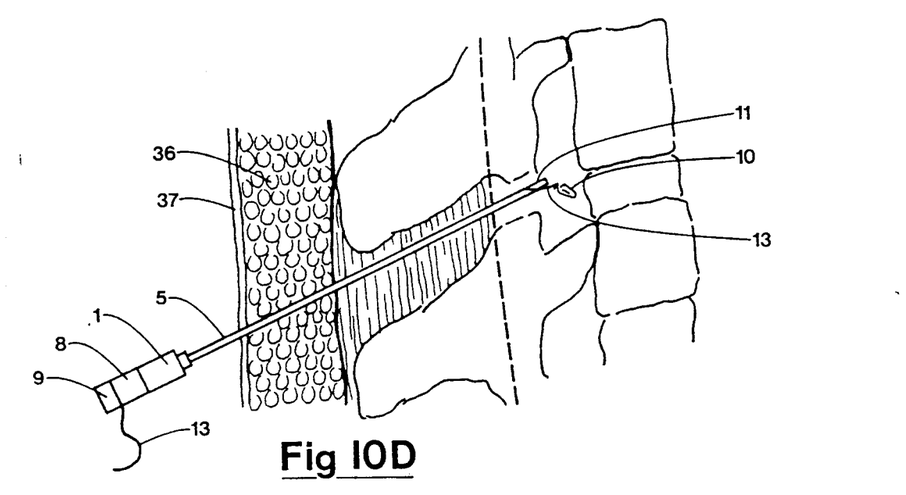
FIG. 10D is a view similar to FIG. 10C showing the dural seal liberated into subarachnoid compartment by the stylet of FIG. 2A.

In FIG. 10D, the end 11 of the stylet 9 contacts the impact cone 15 and pushes the distal sealing means 10 out of the inner cannula 8. Tactically, the stylet 9, about 6 mm from full insertion, will present mild to moderate resistance to the digital push of the examiner. A further push slides the internal parts of the wing assembly 28 along the distal interior cleft 18 of the interior cannula 8 until the impact cone 15 and wing tips are pushed into the subarachnoid space.

Figure 10E:
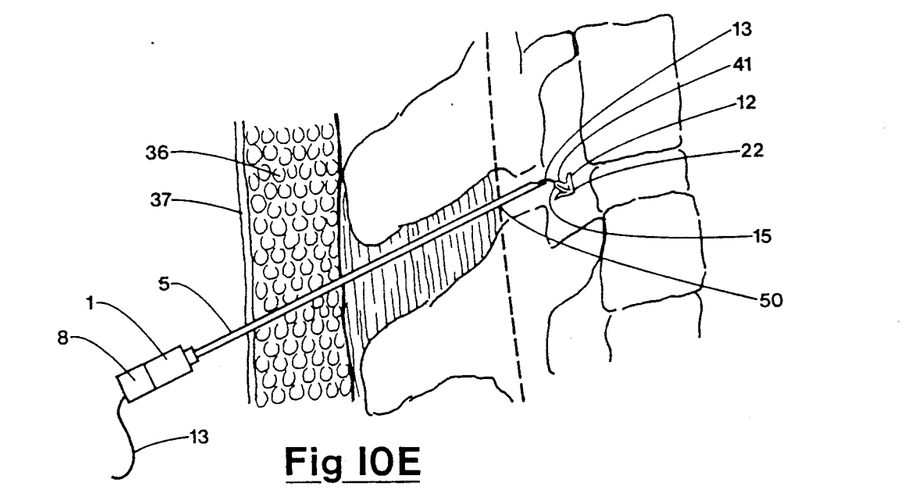
FIG. 10E is a view similar to FIG. 10D illustrating the dry gelatin product and the impact wings of the dural seal spreading.

In FIG. 10E, the previously dry gelatin product sealing component 17 swells and the wings 12 spread open.

Figure 10F:
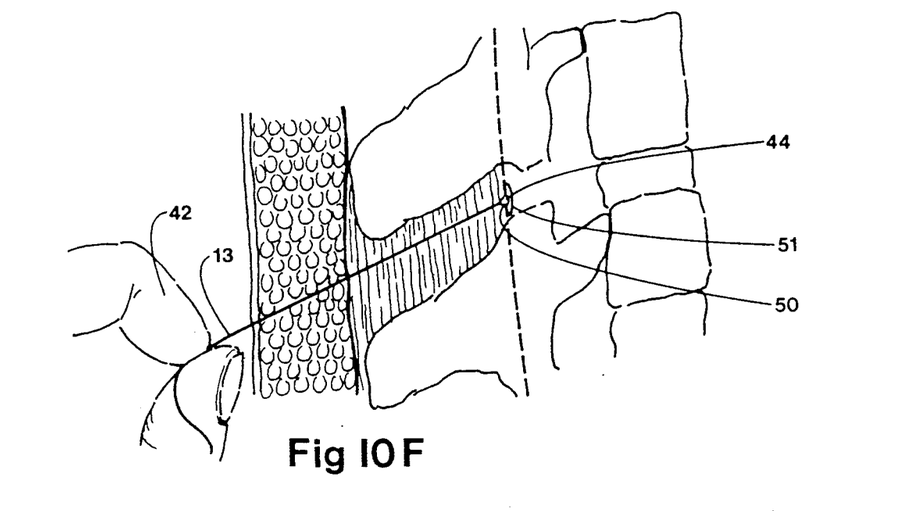
FIG. 10F is a view similar to FIG. 10E illustrating the use of tension on the absorbable suture seating the impact plug of the dural seal into the dural opening.

In FIG. 10F, the stylet 9, the inner cannula 8, and the outer cannula 1 have been removed and the suture 13 has been placed in tension by the examiner 42. The impact plug 15 partially seats in the dural/arachnoid needle defect 50. The wings 23 spread causing the gelatin product to pancake and the wing impact cone 19 seats in the impact cone 15 thereby providing a seal around the puncture 50.

Figure 11B:
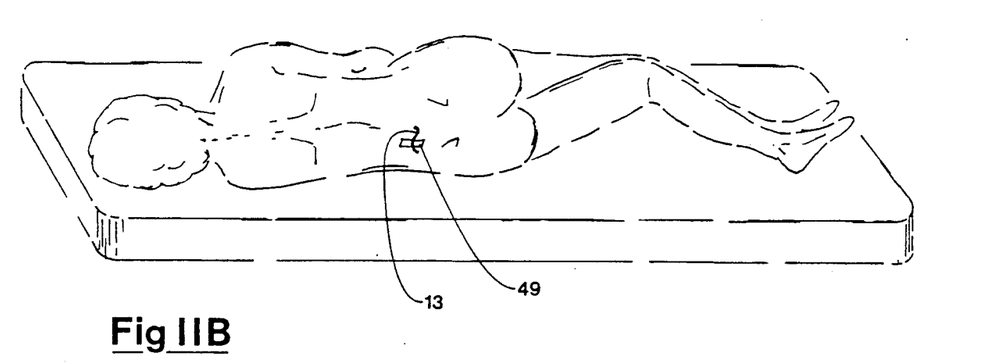
FIG. 11B illustrates the dural sealing means of the present invention in place after lumbar puncture.

The suture 13 is placed on tension for several minutes, such as 3 to 5, by the examiner, and then taped onto the skin as best seen in FIG. 11B.

The dural plug is held in place by the following:
(a) Cerebrospinal pressure 0.3-1.2 PSI (or higher in disease states) directed outward from subarachnoid space 30 holds the gelatin product/wings against arachnoid/dura;
(b) The impact cone (area equals 0.5945 square millimeters fills approximately 50% of the needle defect;
(c) The dry volume of the dry gelatin product is approximately 0.88 cubic millimeters. Assuming the radius of needle defect to be 0.635 mm, this dry volume would cover an opening with a radius of 1.183 mm with a height of 0.2 mm or a radius of 0.8368 mm with a height of 0.4 mm. This is dry volume; water soaked volume is increased by 30-50% allowing ample dry gelatin product volume to fill the needle defect;
(d) Needle tract body clotting mechanism retains absorbable suture tension;
(e) Skin tape 49 provides initial outward tension security.

After several days, such as 5 to 7 days, the absorbable suture 13 drops off.

The present invention, therefore, is well adapted to carry out the objects and attain the ends and advantages mentioned, as well as others inherent therein. While a presently preferred embodiment of the invention has been given for the purpose of disclosure, numerous changes in the details of construction, arrangement of parts, and steps of the process, will be readily apparent to those skilled in the art and which are encompassed within the spirit of the invention and the scope of the appended claims.

What is claimed is:

1. A dural sealing apparatus for spinal puncture and sealing comprising,
    a first cannula for performing a spinal puncture,
    a second cannula and a stylet, said stylet being telescopically received within said second cannula said second cannula being telescopically insertable into said first cannula,
    means for sealing the dura positioned in the distal end of said second cannula including
    a dry gelatin product component which softens and swells in the presence of spinal fluid for sealing the spinal puncture,
    elastic, initially folded, impact wings for packing the softened gelatin product into the spinal puncture, and
    an impact cone for seating in the spinal puncture behind the gelatin product and impact wings, and
    seal actuating means connected with said sealing means extending out of the proximal end of said second cannula, said stylet for pushing said sealing means out of said second cannula.

2. The apparatus of claim 1 wherein the gelatin product is slidably positioned on said actuating means.

3. The apparatus of claim 1 wherein said dural seal means includes the impact cone, the gelatin product component slidably positioned on the seal actuating means, and the impact wings connected to the seal actuating means in sequence.

4. The apparatus of claim 1 wherein the gelatin product component is slidably positioned on the seal actuating means.

5. A method of sealing a spinal puncture comprising, performing a spinal puncture using a first cannula, telescopically inserting a second cannula into the first cannula in which a dura seal is positioned in the distal end of the second cannula and connected to an absorbable seal actuator line, the seal actuator line having an end extending out of the proximal end of the second cannula, the dura seal including an impact cone slidably connected to the seal actuator line, a swellable sealing component adjusted to the impact cone and slidably connected to the seal actuator line, and a resilient wing assembly adjacent the sealing component and connected to the line, including
after pushing the dura seal through the spinal puncture, allowing the sealing component to absorb spinal fluid and swell and the wing assembly to spread,
thereafter placing the seal actuator line in tension to seat the impact cone in the needle defect resulting from the spinal puncture, and
pulling on the seal actuator line to seat the wing assembly against the impact cone to pack the sealing component against the impact cone to form a seal about the needle defect while holding the extended end of the seal actuator line, and
removing the second cannula and placing the extended end of the seal actuator line in tension to set the dura seal.

6. The method of claim 5 including,
securing the end of the absorbable line to the back of the spine.

7. An apparatus for puncturing the arachnoid/dura mater and sealing the opening resulting therefrom comprising,
a first cannula for penetrating the arachnoid/dura mater and through which operations are conducted in the spinal cavity of a patient,
a second cannula for inserting into the spinal cavity through said first cannula,
a dural seal carried on the end of said second cannula for inserting into the spinal cavity through the first cannula comprised of
a suture,
a plurality of wings attached to the suture and carried on said second cannula in a folded position,
a sealing compound which swells upon contact by an aqueous fluid, and
an impact cone threaded on the suture, the sealing compound being threaded on the suture between the impact cone and the folded wings, and
a stylet for insertion into said second cannula for pushing said dural seal out of said second cannula into the spinal cavity, causing the wings of the dural seal to unfold, the sealing compound to swell, and the impact cone to seat in the opening so that the sealing compound will flatten against the impact cone to seal the opening when the suture is pulled.

8. The apparatus of claim 7 wherein the sealing compound is carried on the end of said second cannula within the impact cone and surrounded by the folded wings of said dural seal.

9. The apparatus of claim 7 wherein the outer parts of the wings of said dural seal are turned inwardly for fitting into said second cannula when folded.

10. The apparatus of claim 7 wherein the wings of said dural seal are comprised of a resilient material.

11. The apparatus of claim 10 wherein the outer part of the wings of said dural seal are turned inwardly for fitting into said second cannula when folded and spring outwardly as a result of the intrinsic elasticity of the resilient material comprising the wings when said dural seal is pushed out of said second cannula by said stylet.

12. A method of sealing an opening made by a first cannula in the arachnoid/dura mater of a patient comprising,
inserting a second cannula into a first cannula, the first cannula having punctured the arachnoid/dura mater of a patient, the second cannula carrying a dural seal on the distal end thereof, the dural seal being comprised of
a suture,
a plurality of folded wings,
a sealing compound which swells in the presence of water, and
an impact cone, the wings, sealing compound and impact cone being threaded onto the suture,
pushing the dural seal off of the distal end of the second cannula into the spinal cavity to seat the impact cone in the opening in the arachnoid/dura mater and to allow the sealing compound to swell,
opening the wings, and
pulling on the suture to flatten the sealing compound against the impact cone with the opened wings.

13. The method of claim 12 wherein the suture is secured to the patient to maintain tension on the suture.

14. An apparatus for sealing a spinal puncture comprising,
a first cannula through which operations are conducted in the spinal cavity of a patent,
a second cannula telescopically insertable into said first cannula,
a wing assembly carried on the end of said second cannula in a first, folded position, said wing assembly being comprised of a resilient elastomer,
a suture attached to said wing assembly,
a sealing compound threaded on said suture, and
a stylet for inserting into said second cannula for pushing said wing assembly and said sealing compound off the end of said second cannula into the spinal cavity, allowing said sealing compound to swell and the wings of said wing assembly to spring outwardly to a second, spread position for engaging the swollen sealing compound to spread the swollen sealing compound over the needle defect left by said first cannula after withdrawal of said first cannula from the spinal cavity and pulling on said suture.

15. The apparatus of claim 14 wherein the ends of the wings of said wing assembly are retained within the end of said second cannula when in said first, folded position.

16. The apparatus of claim 14 additionally comprising an impact cone threaded onto said suture for seating in the needle defect when said suture is pulled.

17. The apparatus of claim 16 wherein said sealing compound is threaded onto said suture between said wing assembly and said impact cone.

18. The apparatus of claim 14 wherein said sealing compound is comprised of a gelatin product.

* * * * *